(12) United States Patent
Ghazarian

(10) Patent No.: US 7,350,721 B2
(45) Date of Patent: Apr. 1, 2008

(54) AROMATIC FRAGRANCE DISPENSER

(76) Inventor: Edvin Ghazarian, 1100 N. Central Ave., Apt. 15, Glendale, CA (US) 91202

( * ) Notice: Subject to any disclaimer, the term of this patent is extended or adjusted under 35 U.S.C. 154(b) by 117 days.

(21) Appl. No.: 10/864,983

(22) Filed: Jun. 10, 2004

(65) Prior Publication Data

US 2005/0274818 A1    Dec. 15, 2005

(51) Int. Cl.
*B05B 1/24* (2006.01)
*F23D 11/00* (2006.01)
*F23D 14/00* (2006.01)

(52) U.S. Cl. .................. 239/132.1; 239/101; 239/128; 239/136; 128/203.26

(58) Field of Classification Search .................. 239/34, 239/53, 54, 55, 56, 57, 60, 47; 128/203.26
See application file for complete search history.

(56) References Cited

U.S. PATENT DOCUMENTS

| | | | |
|---|---|---|---|
| 4,133,318 A | 1/1979 | Gross et al. | |
| 4,781,895 A | 11/1988 | Spector | |
| 5,023,020 A * | 6/1991 | Machida et al. | 261/18.1 |
| 5,174,967 A * | 12/1992 | Fukuhara | 422/124 |
| 5,240,487 A * | 8/1993 | Kung | 96/222 |
| 5,359,801 A | 11/1994 | Mattucci et al. | |
| 5,651,942 A | 7/1997 | Christensen | |
| 5,744,106 A | 4/1998 | Eagle | |
| 5,911,955 A | 6/1999 | Fullam | |
| 5,993,748 A | 11/1999 | Wheeler | |
| 6,033,212 A | 3/2000 | Bonnema et al. | |
| 6,503,459 B1 | 1/2003 | Leonard et al. | |
| 6,619,559 B2 * | 9/2003 | Wohrle | 239/34 |
| 6,761,164 B2 * | 7/2004 | Amirpour et al. | 128/203.26 |

FOREIGN PATENT DOCUMENTS

WO    WO 01/64257 A1    9/2001

\* cited by examiner

*Primary Examiner*—Kevin Shaver
*Assistant Examiner*—James S. Hogan

(57) ABSTRACT

A fragrance dispenser comprises a receptacle for receiving an aromatic substance to be heated; and a heat exchanger connected to the receptacle for heating air upstream of the receptacle, the heat exchanger having means for agitating the air as it is heated and passes therethrough.

26 Claims, 7 Drawing Sheets

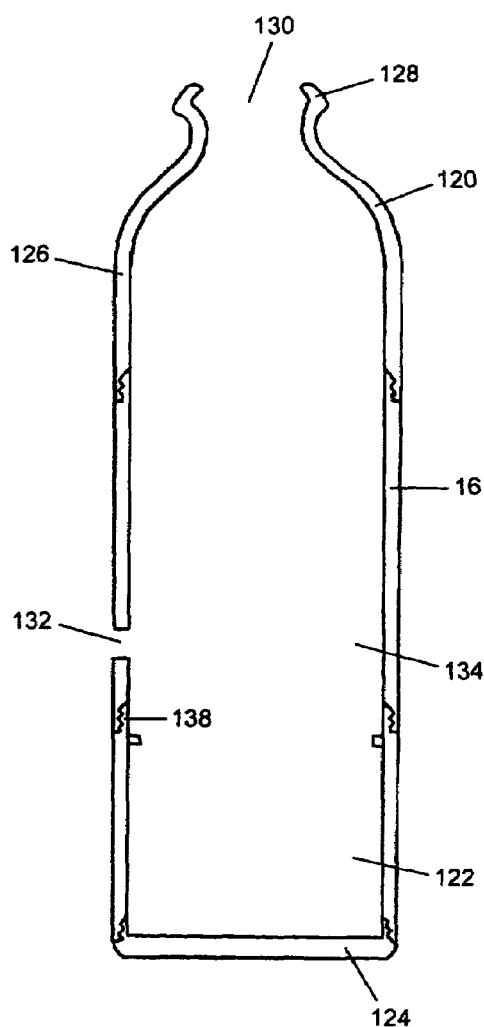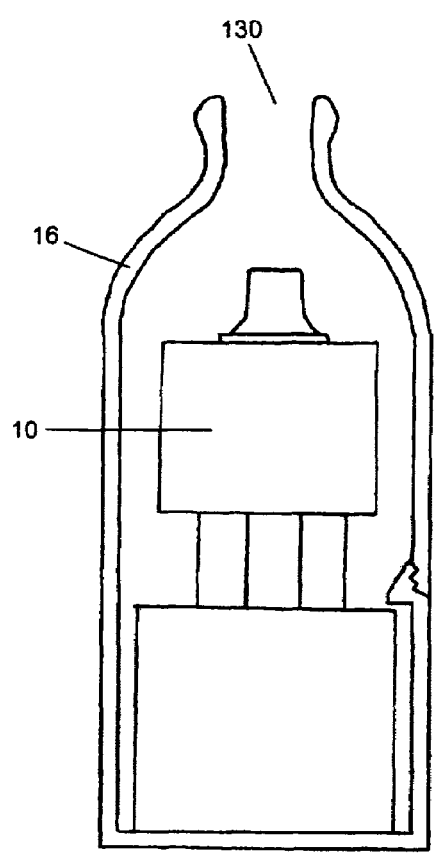
FIG. 6
FIG. 7

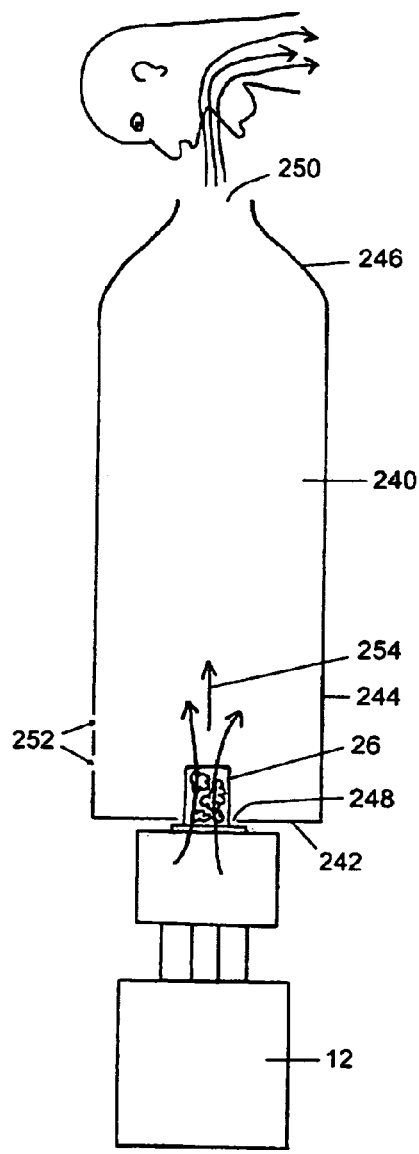
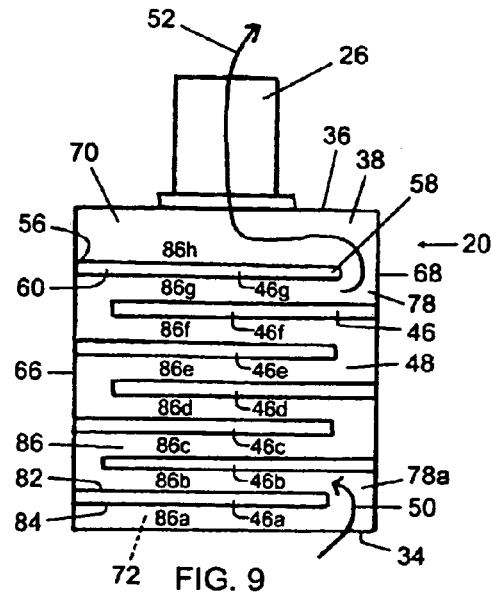
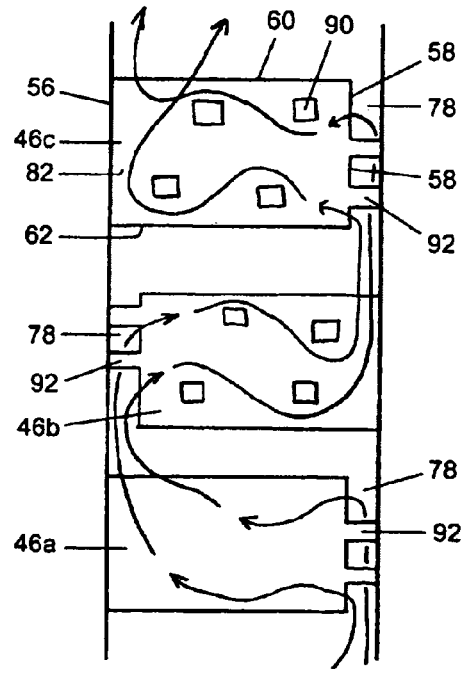
FIG. 8
FIG. 9
FIG. 10

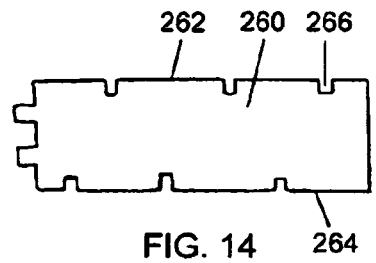
FIG. 14
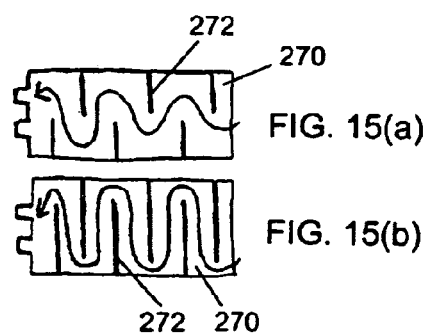
FIG. 15(a)
FIG. 15(b)
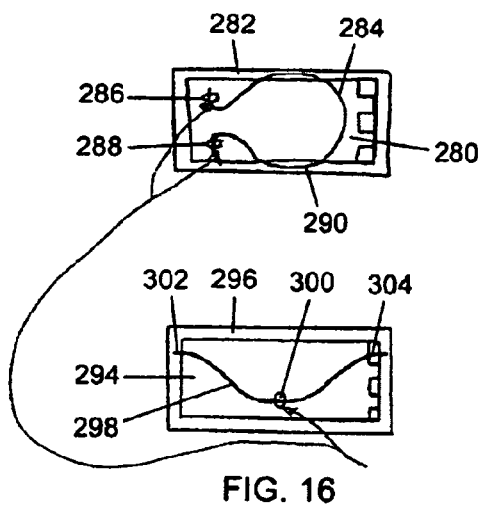
FIG. 16
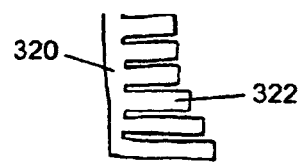
FIG. 18
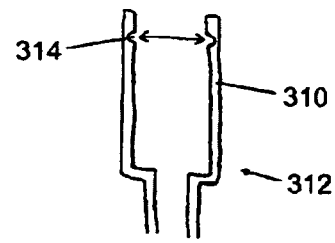
FIG. 17
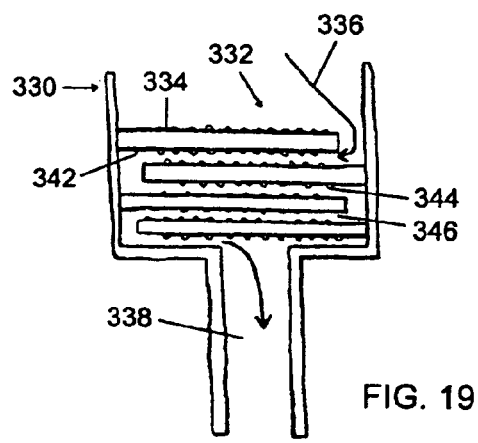
FIG. 19
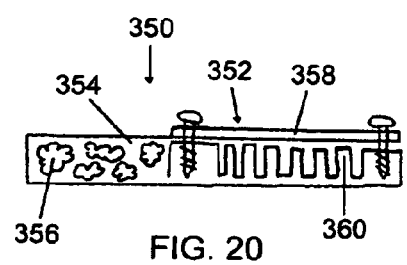
FIG. 20

AROMATIC FRAGRANCE DISPENSER

FIELD AND BACKGROUND OF THE INVENTION

This invention relates to an aromatic fragrance dispenser. Particularly, the invention is for an instrument or device which is able to receive a material capable of giving off a fragrance, conveying heated air through a heat exchanger, heating the material and dispensing the aromatic fragrance in the heated air into the surrounding atmosphere.

A significant variety of instruments or devices are shown in the patent literature for dispensing fragrance produced by a desired material. Essentially, many of these devices comprise a mechanism for heating the material, and some form of passageway for discharging heated air including the desired aromatic fragrance into the atmosphere.

U.S. Pat. No. 4,133,318 (Gross) teaches a water pipe for smoking organic materials, the water pipe including an electric heating element, a chamber for collecting the smoke of the burning product, and a further chamber for cooling the smoke when drawn therethrough.

U.S. Pat. No. 6,503,459 (Leonard) discloses a heated, volatile dispenser which has a closed heating chamber with a ceiling and exit vents. Hot combustion products from a fuel burner pass through a holder, and directly heat a volatile carrier.

U.S. Pat. No. 5,651,942 (Christensen) teaches an aromatic fragrance generator which includes a bulb in a support base, and a fragrance base located in a heating pan. The heated fragrance supplies a pleasant aroma to the atmosphere, and is used primarily to eliminate bathroom and kitchen odors.

U.S. Pat. No. 5,993,748 (Wheeler) teaches a hot gas extraction device, including a container for holding material. A non-flame type heating unit is disposed in a chamber of the device for heating gas. Gas passes through holes, and is discharged from the container.

U.S. Pat. No. 5,744,106 (Eagle) discloses a heated scent dispenser comprising a reservoir heated by igniting paraffin or some other fuel. A chamber contains a fluid reservoir which can be filled with a scent.

U.S. Pat. No. 5,359,801 (Mattucci) teaches a scent and dispenser including a housing for a burner which heats the scent source in a reservoir which causes the scent source to volatalize. The housing is provided with at least one opening to allow for admission of air into a chamber defined by the housing.

U.S. Pat. No. 4,781,895 (Spector) discloses a candle-powered aroma generator, in a lantern format, which uses a scentless candle to create various aromas. A candle is placed below an aroma cartridge, and the simple act of heating provides the aroma.

SUMMARY OF THE INVENTION

In accordance with one aspect of the invention, there is provided an aromatic fragrance dispenser which includes a receptacle or portion which receives a material which, when heated, provides a desired fragrance. Air is heated in a heat exchanger to facilitate thorough mixing and turbulence to increase the consistency of the heated air. The heated air is passed through or over the material and the mixture of the heated air and fragrance is then discharged into the surrounding atmosphere. As such, the invention essentially comprises a means for providing heat, a heat chamber and heat exchanger in which heated air is thoroughly mixed, and a fragrance receptacle over which the heated air is conducted to provide an aromatic fragrance to the heated air. The heated air/fragrance mixture is then discharged from the device into the ambient atmosphere to provide a pleasing fragrance of the desired type. The desired type of fragrance is, of course, determined based on the nature of the material selected for placement in the fragrance container or receptacle.

Raw plant material in any form, including, but not limited to, roots, stems, leaves, buds, seeds, fruits, vegetables and herbs can be placed inside of the receptacle to produce a fragrance.

In one form, the instrument in which the fragrance is placed, and the heat exchanger, may be inserted into some form of receptacle which has apertures or openings so that a stream of air can be created within the receptacle or container, wherein the stream of air, including the heated air and fragrance mixture, can be discharged into the ambient atmosphere.

According to one aspect of the invention, there is provided a fragrance dispenser comprising a receptacle for receiving an aromatic substance to be heated; and a heat exchanger connected to the receptacle for heating air upstream of the receptacle, the heat exchanger having means for agitating the air as it is heated and passes therethrough.

The means for agitating may comprise a plurality of plates. Preferably, the plates are arranged in a stacked, substantially parallel arrangement, wherein a channel is formed between adjacent plates, and the plurality of plates define an air flow path through the heat exchanger along the channels.

Preferably, each plate has an upper and lower surface, and turbulence producing structures are formed on at least one of the upper and/or lower surfaces. The turbulence producing structures may comprise a plurality of projections extending upwardly from the upper and/or lower surface of the plate.

In one preferred form, the receptacle comprises a container downstream of the heat exchanger. The receptacle may comprise a removable tray which can be inserted in the path of air discharged from the heat exchanger, the removable tray having a handle to facilitate insertion and removal of the tray.

An ejection mechanism for ejecting used aromatic substance from the receptacle may be provided. The ejection mechanism may be a spring-loaded shaft, one end of which is a adjacent the receptacle, and the other end of which comprises a button for activation by the user.

The dispenser may further comprise a thermometer for monitoring and displaying the temperature in the heat exchanger. The thermometer may be a digital thermometer located in a handle housing adjacent the heat exchanger, the digital thermometer having a sensor or probe in the heat exchanger.

Preferably, the dispenser may further comprise an aroma dispersal container for releasably receiving at least a portion of the dispenser, the aroma dispersal container containing at least one aperture through which aromatic air produced by the dispenser can be discharged into the surrounding atmosphere.

According to another aspect of the invention, there is provided a method for producing an aroma from an aromatic substance, comprising placing the aromatic substance in a receptacle to be heated, attaching a heat exchanger to the receptacle for heating air upstream of the receptacle, and agitating the air as it is heated, and passing the heated air over the aromatic substance.

BRIEF DESCRIPTION OF THE DRAWINGS

In the drawings:

FIG. 6 is a cross-section through a container component for the aromatic fragrance dispenser shown in FIG. 1 of the drawings;

FIG. 7 is a cross-section showing the aromatic fragrance dispenser within a dispensing receptacle;

FIG. 8 shows another embodiment of a dispensing component for the aromatic fragrance dispenser in accordance with one embodiment of the invention;

FIG. 9 is a schematic cross-section showing details of the heat exchanger portion of the aromatic fragrance dispenser in accordance with one aspect of the invention;

FIG. 10 is a schematic representation showing three plates of the heat exchanger in accordance with one aspect of the invention;

FIG. 14 shows a top view of a single plate of the heat exchanger component in accordance with one embodiment of the invention;

FIGS. 15(a) and 15(b) show a pair of plates which can be used in accordance with another embodiment of the invention;

FIG. 16 shows a pair of plates fastened in position using a spring, in accordance with one aspect of the invention;

FIG. 17 shows a schematic representation of a heating component including grooves to facilitate the holding in position of plates of the heat exchanger in one form of the invention;

FIG. 18 shows a schematic representation of the heat exchanger including spacers for holding plates in desired spaced orientation;

FIG. 19 is a schematic cross-section through the heat exchanger of the aromatic fragrance dispenser in accordance with another aspect of the invention;

FIG. 20 shows a further embodiment of the heat exchanger component of the aromatic fragrance dispenser;

DETAILED DESCRIPTION OF THE PREFERRED EMBODIMENTS

Figure 1:
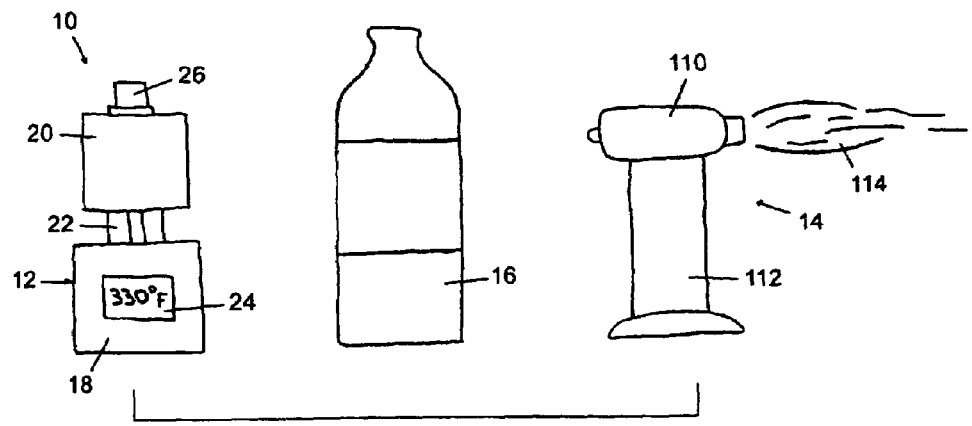
FIG. 1 is a general view of the aromatic fragrance dispenser, and various components thereof, in accordance with one embodiment of the invention.

In the drawings, various embodiments of the invention are illustrated and described herein. The invention may comprise a number of components. A central component is the heat chamber, in which the material or composition providing the fragrance may be disposably contained. However, the invention may also comprise a heating source for providing the necessary heat to the heat chamber. Furthermore, the invention may comprise the additional component in the form of a container, the container being configured to receive the heat chamber, and having apertures and/or passageways through which a stream of air may be conveyed, the passageways discharging into the ambient atmosphere so that air containing the fragrance can be placed at the desired location.

Reference is now made to FIG. 1 of the drawings, which shows schematically each one of the three components of the invention mentioned above. In FIG. 1, there is shown an aromatic fragrance dispenser 10 comprising a heating component 12, a heating source 14, and a container 16. It will be appreciated that not all embodiments of the invention require the container 16, and different heating components and heating sources may be provided.

Figure 3:
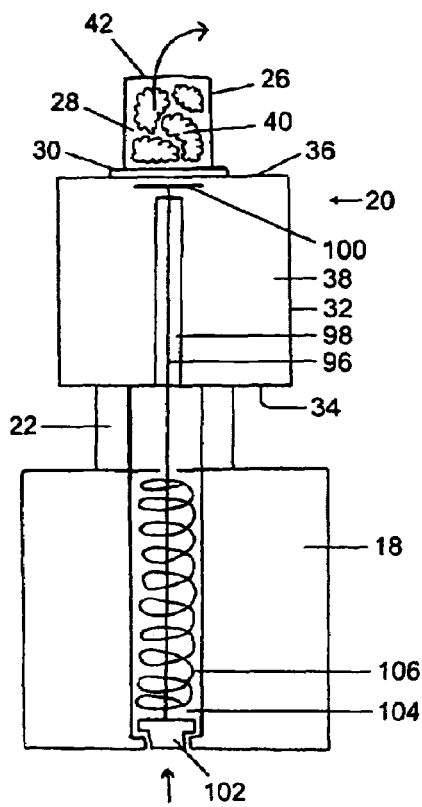
FIG. 3 is a cross-section through a portion of an aromatic fragrance dispenser as shown in FIG. 1 of the drawings.
Figure 4:
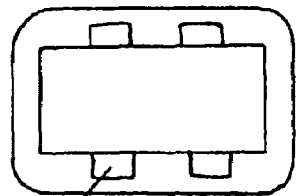
FIG. 4 is a top view of the aromatic fragrance dispenser shown in FIG. 3 of the drawings.
Figure 5:
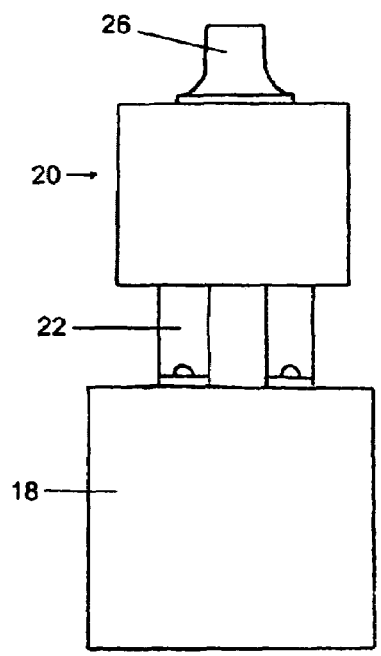
FIG. 5 is a front view of the aromatic fragrance dispenser shown in FIG. 3 of the drawings.

The heating component 12 shown in FIG. 1 of the drawings comprises a holder housing 18, a heat exchanger 20, and four connector posts 22 for securing the holder housing 18 to the heat exchanger 20. A more detailed view of the heating component 12 shown in FIG. 1 of the drawings is shown in FIGS. 3, 4 and 5.

The holder housing 18 generally includes a thermometer 24 for providing an indication of the temperature of the air within the heat exchanger 20. The thermometer 24 will have an appropriate probe or sensor located within the heat exchanger 20, so that the temperature, as it changes as a result of heat supplied from the heating source 14, is monitored and displayed on the thermometer 24.

At the top of the heat exchanger 20, there is provided an outlet 26. The outlet 26 forms a chamber 28 having a base 30. The heat exchanger 20 itself comprises side walls 32, a base wall 34, and a top wall 36. The base 30 of the outlet 26 rests on the top wall 36 of the heat exchanger 20. The chamber 28 is in communication with the interior 38 of the heat exchanger 20, and heated air exiting the heat exchanger 20 thus passes through the chamber 28, as will be described further below.

The chamber 28 is able to receive an aromatic substance 40, which is disposed within the chamber 28 so that heated air passing therethrough acquires the fragrance or aroma of the aromatic substance 40. The outlet 26 has an opening 42 at the top thereof through which the air incorporating the aroma from the aromatic substance 40 is discharged.

The interior 38 of the heat exchanger 20 comprises a series of substantially parallel plates, best seen in FIG. 9 of the drawings. In FIG. 9, the interior 38 of the heat exchanger 20 shows seven plates 46, and the plates are arranged in a specific configuration so as to provide an air pathway, designated by the reference numeral 48 through the interior 38 of the heat exchanger 20. The heat exchanger 20 receives heat from an outside source, to be described, and heats the air in the interior 38, which moves along the air pathway in the direction of arrow 50. Ultimately, the heated air exits through the outlet 26, as shown by arrow 52. The purpose of the plates 46 within the interior 38 is to provide thorough mixing of the air as it is heated and passes through the interior 38 and outlet 26. The presence of the plates 46 provides shear and turbulence to facilitate thorough mixing and consistency of the air temperature as it passes through the outlet 26, and particularly the aromatic substance 40, which in turn provides for an enhanced fragrance or aroma exiting the heat chamber 12.

Each plate 46 has an attachment end 56, a free end 58, and side walls 60 and 62.

The side wall 32 of the heat exchanger 20 is made up of a side wall 66, and a side wall 68. Further, the heat exchanger 20 has a front wall 70 and a rear wall 72. The sides walls 66 and 68, front wall 70 and rear wall 72 define the interior 38 of the heat exchanger 20. The interior 38 is closed off on the top by top wall 36, and by the bottom wall 34.

It will be seen that each alternate plate 46 has its attachment end 56 attached to or against side wall 66, while the other alternate plates 46 have their attachment ends 56 connected to or against the side wall 68. An open space or gap 78 is formed between the free end 58 of each plate and the particular side wall to which it is adjacent. Further, the sides 60 and 62 of each plate 46 abut against or are connected to the front wall 70 and rear wall 72 respectively. The attachment of each plate 46 within the interior 38 is such that air will generally be incapable of passing between the respective plates 46 and the front wall 70 and rear wall 72, as well as the connection between the attachment end 56 of the plate and the side wall to which it is attached. Thus, the stream of air passing through the heat exchanger 20 will only be able to pass between plates 46 and through the open spaces 78.

Each plate 46 has an upper surface 82 and a lower surface 84. A channel 86 is formed between the upper surface 82 of one plate 46, and the lower surface 84 of its adjacent plate 46.

From the above description, the passage of air through the heat exchanger 20 can be described as follows: Air enters the interior 38 into channel 86a through the base wall 34. The air then passes through the open space or gap 78 to enter the channel 86b. In similar fashion, the air passes through channels 86c to 86h, passing around each open space 78, and is eventually discharged through the outlet 26. It will be appreciated that each plate, other than at its open space 78, is sufficiently connected or close to the walls of the heat exchanger 20 so that air cannot pass through the heat exchanger 20 except around the open spaces or gaps 78.

While the embodiment shown in FIG. 9 of the drawings shows seven plates, any number of plates can be used within the interior 38, according to the needs and requirements of the heat component 12. Typically, there will be between about six and twelve plates, but fewer or more such plates may be used within the scope of the present invention.

Preferably, the heat exchanger 20, as well as the plates 46 contained therein, are comprised of metal, and preferably are made of a high quality aluminum. This facilitates a high heat conductivity, as well as an enhanced ability to store heat. While the plates are preferably comprised of such metal, other materials may be used which will effectively result in the necessary exchange of heat in accordance with this invention.

The holder housing 18 of the heat component 12 may be made of wood, plastic, or such other material suitable in the circumstances. Of course, one advantage of using wood, is that it will not become hot, so that the heat component 12 can be handled using the holder housing 18 without the user becoming burned. The thermometer 24, preferably in the form of a digital thermometer, is contained within the housing 18 so that the necessary display can be easily viewed by the user. As mentioned, the thermometer 24 will have a probe or other form of sensor which extends into the heat exchanger 20, so that the temperature at a desired point therein can be monitored and reflected on the display on the thermometer 24.

The plates illustrated in FIG. 9 of the drawings are of one type only, and will typically have relatively smooth upper surfaces 82 and lower surfaces 84. However, many different configurations of these plates 46 may be provided to provide improved or enhanced turbulence of the air passing through the channels 86. One such arrangement can be seen in FIG. 10 of the drawings. FIG. 10 of the drawings shows three plates 46a, 46b and 46c, typically arranged one above the other, but rotated so as to provide a schematic representation of the configuration. The plate 46a has an upper surface 82, and four projections, each having a reference numeral 90, extending upwardly from the upper surface 82. Each plate 46a, 46b and 46c has the open space or gap 78 by means of which air can pass upwardly between the plates. Plates 46a and 46c have this gap 78 on one side, while the intermediate plate 46b has the gap 78 on the opposing side.

In FIG. 10, each plate 46a, 46b and 46c has the free end 58. Each free end 58 has a pair of tabs 92 extending outwardly therefrom, which abut against the side walls 66 or 68 of the heat exchanger 20. These tabs 92 help to stabilize the position of the plates 46a, 46b and 46c, and position them more accurately within the interior 38, and also create turbulence by standing in the way of the air flow, but not blocking it. The arrows show the direction of air movement between the plates 46a, 46b and 46c in FIG. 10. It will be seen that the projections 90 on the upper surface 82 of each plate increases turbulence and shear so that the thorough mixing of the air, ensuring consistency of temperature, may be achieved. While FIG. 10 shows four projections 90 on the upper surface of each plate, it will be appreciated that the invention not limited to four such projections. In fact, there may be any such number of projections as appropriate, and the projections may alternatively, or additionally, be formed on the lower surface 84 of each plate. Further, each projection 90 may extend outwardly from its surface only a short distance into the channel, or it may extend the full distance from the upper or lower surface of its own plate, to the lower or upper surface of an adjacent plate. Furthermore, the positioning of each projection 90 may change, and may be selected so as to interact with projections on other plates, and to help achieve optimal mixing of the heated air.

As shown in FIG. 3 of the drawings, a mechanism is provided whereby used or spent aromatic substance 40 contained within the chamber 28 can be easily expelled. One such mechanism includes a tamping rod 96 extending through the length of the aromatic fragrance dispenser. The tamping rod 96 includes an elongate shaft 98 terminating in a shelf 100 at the upper end thereof. A button 102 is formed at the lower end of the shaft 98. The tamping rod 96 is accommodated within a passage 104 which extends through the entire aromatic fragrance device 10. A spring 106 tends to urge the tamping rod 96 in a downward direction, so that the shelf 100 is generally held below the aromatic substance 40. Once the aromatic substance 40 has been used, and needs to be discharged through opening 42, the user depresses the button 102 against the bias of the spring 106, thereby moving the shelf 100 upwardly into the chamber 28 and is pushed sufficiently far so as to discharge any used aromatic substance 40 from the chamber 28. Once the button 102 is released, the spring 106 will urge it into its normal rest position so that the shelf 100 does not interfere with insertion of fresh aromatic substance 40, or with the flow of air through the heat exchanger 20.

The air in the heat exchanger 20 may typically be heated by a heating source 14, shown in FIG. 1 of the drawings. A wide variety of such heating sources may be provided, and the heating source 14 shown in FIG. 1 typically comprises a container 110 for a combustible material, and a base 112. The combustible material may be any desired or suitable fuel. Ignition of such fuel produces a flame 114, which may be varied, and the flame 114 applied externally to the heat exchanger 20 for the purposes of heating the air therein.

FIG. 1 also shows the container, illustrated in more detail in FIGS. 6 and 7 of the drawings. The container 16 comprises an upper portion 120, which may be threadedly secured to a lower portion 122. The container 16 has a base 124, side walls 126 and a top 128. An aperture 130 is provided in the top, and an aperture 132 also provided in the side wall 126. The container 16 has a chamber 134.

When the upper portion 120 is removed from the lower portion 122, by rotation at the threaded connection 138, the aromatic fragrance dispenser 10 can be inserted therein, and the container 16 closed, one embodiment of which is illustrated in FIG. 7 of the drawings. FIG. 7 of the drawings, is for a slightly different dimensioned container 16, but this serves to illustrate the flexibility and breadth of the invention in that the container 16 may be of a widely varying dimension and configuration.

Figure 2:
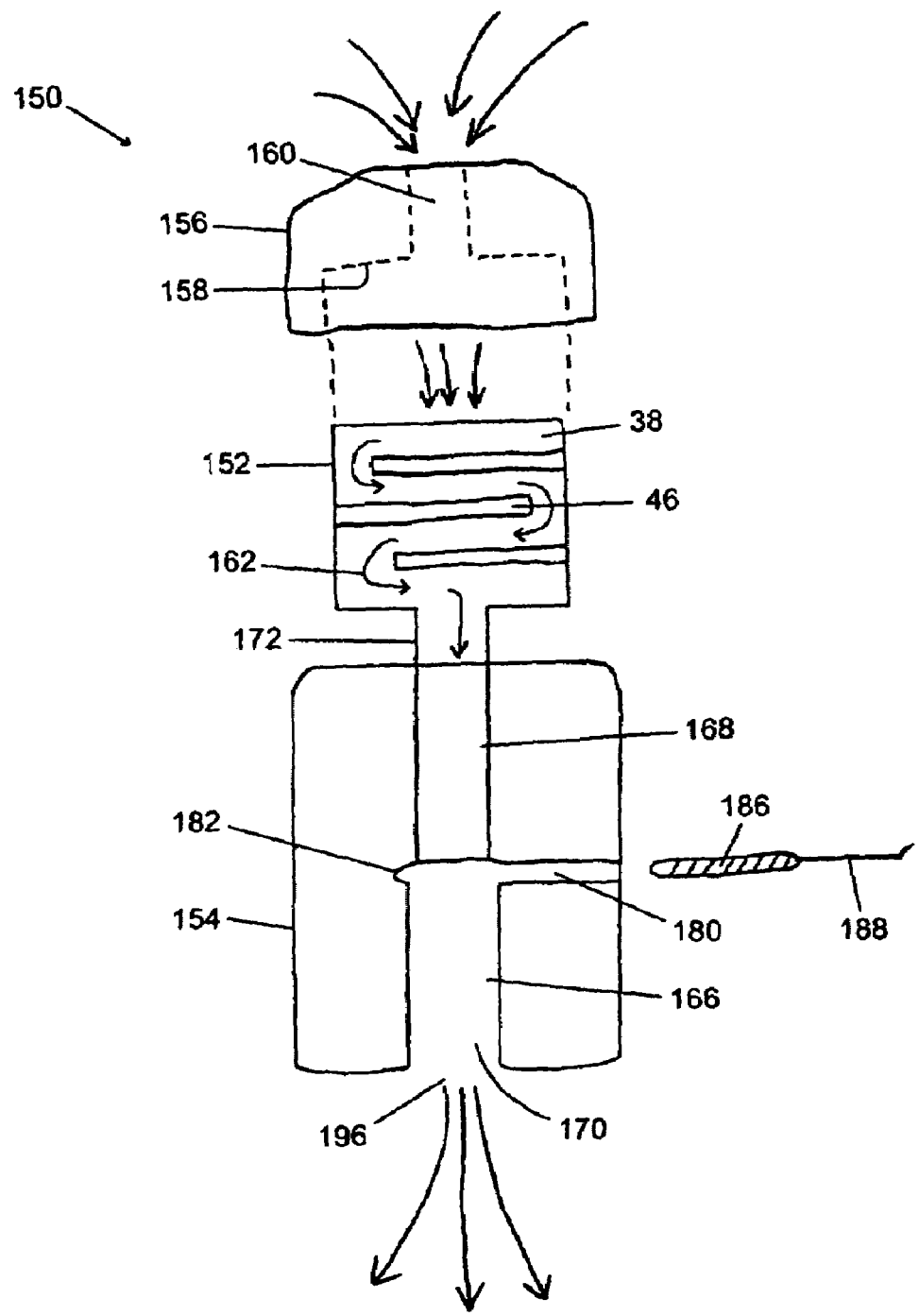
FIG. 2 is a cross-section through another embodiment of an aromatic fragrance dispenser of the invention.

When the dispenser 10 is inserted in the container 16, after heating the heat exchanger and releasing the aromatic substance 40, the dispenser 10 can be moved around within the container 16, and air can be blown in through the aperture 130, by the mouth of the user, so that and air flow is formed within the chamber 134, and the air exits through the aperture 132. It will be appreciated that the air exiting through the aperture 132 will incorporate the aroma or fragrance given off by the aromatic substance 40, and the movement and dispensation of air from the container through the aperture 132 can thus be controlled to provide the necessary fragrance to a desired area. Also, the fragrant air in the container can simply be allowed to diffuse out through the openings Reference is now made to FIG. 2 of the drawings which shows a different embodiment of the aromatic fragrance dispenser of the invention. FIG. 2 shows an exploded view of a dispenser 150, the dispenser 150 generally comprised of a heat exchanger 152 and a base housing 154. The heat exchanger 152 includes various side and front walls, as has already been described above, and a series of plates 46 contained in the interior 38, in much the same way as described above. The different configurations of the plate described may be used equally in different variations and combinations within the interior 38.

A cap 156 fits on the top of the heat exchanger 152, the cap 156 having an internal recess 158, which corresponds to the shape of the heat exchanger 152, and can be releasably attached and released therefrom. Further, the cap 156 includes an inlet passage 160. Air thus flows from the inlet passage 160 to the recess 158, and thereafter enters the interior 38 of the heat exchanger 152, where the air is heated and moves through the heat exchanger 152 in the general direction as shown by the arrows 162.

The base housing 154 comprises a substantially central core channel 166 running therethrough. The core channel 166 includes an upper portion 168, and a lower portion 170. The heat exchanger 152 has depending therefrom a tubular extension 172 which is inserted, and is received snugly within, the upper portion 168 of the channel 166. In this way, the heat exchanger 152 is releasably connected to the base housing 154.

A transverse passage 180 extends through a part of the base housing 154. The transverse passage 180 is in communication with the core channel 166, as it transitions from the upper portion 168 to the lower portion 170. An indent 182 is formed in the base housing 154 approximately opposite the transverse passage 180.

The base housing 154 further comprises a tray 186, substantially flat, and a handle 188 extending from the tray. The tray 186, in use, is adapted to receive an aromatic fragrance material. The tray 186 can be inserted and removed from the base housing 154 by sliding it through the transverse passage 180. When fully installed, the tray 186 will occupy the core channel 166, so that all air flowing therethrough will have to pass through the tray 186, and any fragrant substance therein. This can best be seen in FIG. 11 of the drawings. The indent 182 is designed so as to receive one end of the tray 186 so that it fully spans the diameter of the core channel 166. The handle 188 attached to the tray 166 is of sufficient length so that it extends through the transverse passage 180 when the tray 186 is in its installed position, and the end of the handle 188 can still be grasped so that removal of the tray 186 can be effected. A string or flexible grasp 192, best shown in FIG. 11 of the drawings, may be provided so that the initial removal of the tray 186 can be more conveniently effected.

In use, the airflow through the dispenser 150 is such that air is introduced through the inlet passage 160, passes into the interior 38, and is heated in the heat exchanger 152. The air passes over the plates 46, which provide shear, turbulence and thorough mixing to ensure consistency, and is eventually discharged into the tubular extension 172, and thereafter into the core channel 166. The heated air passes over the tray 186, and hence the aromatic material, and thereafter exits through discharge opening 196, into the ambient atmosphere to provide the desired fragrance. Once the aromatic material in the tray 186 has been used, it can be removed by pulling out the tray 186, disposing of the material, after which new aromatic or fragrant material can be inserted.

Figures 11, 12, 13:
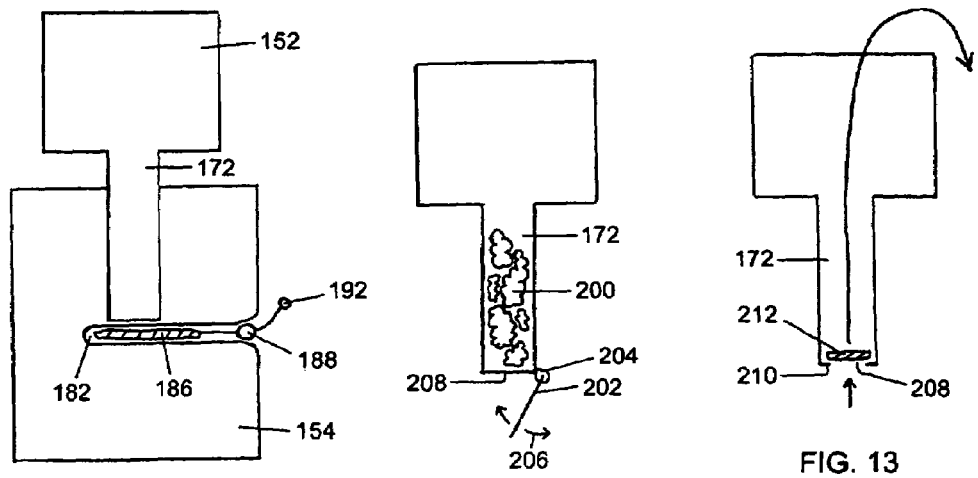
FIG. 11 shows a schematic representation of the heat exchange component of the aromatic fragrance dispenser, showing one embodiment for inserting the fragrance material.
FIG. 12 shows a schematic representation of the heat exchange component of the aromatic fragrance dispenser, showing another embodiment for inserting the fragrance material.
FIG. 13 shows a schematic representation of the heat exchange component of the aromatic fragrance dispenser, showing yet another embodiment for inserting the fragrance material.

Variations of the embodiment in FIG. 2 may be provided, and two such variations are illustrated in FIGS. 12 and 13 of the drawings. In FIG. 12, the aromatic material 200 is inserted into the tubular extension 172, and a screen 202, hinged at pivot point 204, can be opened and closed as shown by the arrows 206. When the aromatic material 200 is inserted, the screen 202 is moved to the closed position so that the aromatic material cannot fall out of the tubular extension 172. An appropriate closing mechanism, which may be in the form of a clamp, snap fastener, hook or any other form may be provided to keep the screen 202 in the closed position. After use, the screen 202 is moved to the open position so that the spent aromatic material 200 can simply be disposed of through the opening 208 in the tubular extension 172.

In FIG. 13, the opening 208 of the tubular extension 172 has an inwardly directed annular flange 210 which receives a screen 212. The edges of the screen 212 rest on the flange 210, and the aromatic material can be placed above the screen. The screen once used may be pushed out through the heat exchanger 152.

In FIG. 8 of the drawings, a container, in accordance with a further embodiment of the invention, is illustrated. In FIG. 8, there is shown a heating component 12, of the type illustrated in FIG. 1 of the drawings. However, the heating component 12 can be of any other configuration in accordance with the invention, and the one depicted in FIG. 1 of the drawings is shown for illustrative purposes only. In this case, a container 240 having a base 242, side walls 244 and a top 246 is shown. An aperture 248 is formed in the base 242, and is configured so as to receive the outlet 26 of the heat chamber 12. The top 246 of the container 240 has an opening 250, and the lower portion of the side wall 244 may have apertures 252. A suction provided over the opening 250 induces air from the heating component 12, as indicated by arrow 254. Further, if apertures 252 are present, the air, which has the acquired fragrance or aroma from the aromatic substance, may be combined with incoming ambient air through the apertures 252 and mixed therewith. The aromatic-laden air, whether combined with ambient air through apertures 252 or not, is then blown out through the opening 250, and may enter the surrounding environment to provide the desired fragrance.

After the aromatic-laden air is drawn into container 240 by opening 250, the aromatic-laden air is blown out by blowing into opening 250. Also, the fragrant air in the container can simply be allowed to diffuse out through the openings.

The advantage of the container, which may preferably be comprised of plastic, is to hold the aroma which can later be blown around a space. Alternatively, the container may simply sit, so that the aroma diffuses naturally through a space.

FIGS. 14 through 17 of the drawings show different configurations of the plates, and possible connection types to the heat exchanger 20. FIG. 14 shows a plate 260 having side edges 262 and 264. Each side edge 262 and 264 has spaced indents 266. It will be noted that the indents 266 along side edge 262 are not directly opposite the indents 266 along side edge 264. While this is a specific embodiment of the invention, it will be appreciated that the plates may have any number of these detents along side edges, and may be arranged in many ways with respect to each other.

The purpose of the indents 266 is to receive a vertical rail on the inside surface of the heat exchanger. Thus, for the plate shown in the embodiment in FIG. 14, three rails will be present on each side of the heat exchanger, each rail receiving an indent 266. The rails on opposite sides of the heat exchanger would be oriented so as to receive the indents on each side of the plates 260. The presence of rails extending up the inside surface of the heat exchanger is another mechanism whereby the plates 260 can be more accurately located and held in position. Since it is contemplated that these plates be removable for cleaning, and reinsertable thereafter, the invention preferably includes mechanisms and structures, such as the indents and rails, to assist the user in quickly and carefully dismantling the plates, and then reinserting them quickly in an accurate and precise manner.

With reference to FIGS. 15(*a*) and 15(*b*), a different surface configuration of a plate 270 is shown. Both of the plates 270 shown in FIGS. 15(*a*) and 15(*b*) have transverse walls, which may be of varying height to straddle substantially much or all of a channel 86, or only extend slightly above the surface of the plate. In FIG. 15(*a*), one plate 270 has transverse walls 272 which extend to approximately the mid-part of the plate 270, while in FIG. 15(*b*) another plate 270 shows transverse walls 272 extending most, but not all, of the distance across the plate. Of course, the dimensions of the transverse walls 272 will affect the turbulence and mixing properties of the plates 270. As will be seen from the arrows representing the air flow path over the plates 270, air will be diverted around the transverse walls, or at least some of the air will be so diverted, so that additional turbulence, shear and mixing takes place.

FIG. 16 shows two plates which are held in position by a resilient spring steel wire. In FIG. 16, a plate 280 is located within a heat exchanger 282. A steel spring wire 284 connects to one of the surfaces of the plate 280 at connection points 286 and 288. The spring 284 has a generally circular shape, and has portions 290 which extend beyond the edge of the plates 280. These portions 290 engage in a slot or recess within the heat exchanger 282, thus providing support for the plate 280 within the heat exchanger 282.

Also in FIG. 16, there is shown a plate 294 in heat exchanger 296, the plate 294 including a spring 298 secured to the plate at a connecting point 300. The spring 298 has a pair of ends 302 and 304 which engage in holes, recesses or the like in the heat exchanger 296, to secure the plate 294 within the heat exchanger 296.

FIG. 17 of the drawings shows schematically, in cross-section, the side walls 310 of a heat exchanger 312. The side walls 310 are shown to include an indent 314, the indent 314 capable of receiving the spring 284, or the spring 298, as shown in FIG. 16 of the drawings.

In FIG. 18 of the drawings, there is shown schematically, in side view, a rail 320 and a series of spacers 322 extending outwardly from the rail 320. Such a rail 320 and spacers would extend inwardly from the heat exchanger. The rail 320 would typically engage one of the indents 266, such as those shown in FIG. 14 of the drawings, while the spacers 322 would provide the necessary mechanism to ensure consistent spacing between the series of plates which may be arranged in a layer or stacked form within the heat exchanger.

The spacers 322 also provide turbulence and mixing, and can be varied in length to provide maximum heat transfer efficiency. The longer a spacer 322 is, the more turbulence and agitation of the air will be created and cause more heat to be transferred than a shorter spacer 322.

FIG. 19 of the drawings shows a further embodiment of the invention, comprising a heat exchanger 330 having an interior space 332 with a series of plates 334. Air enters the heat exchanger 330 as indicated by arrow 336, travels over the plates for turbulence and thorough mixing, and exits into the tubular extension 338. It will be noted that each plate 334 has an upper surface 340 and a lower surface 342 on which are arranged a series of protuberances 344. These protuberances 344 extend into the channel 346, defined between each pair of adjacent plates, and result in increased turbulence and agitation of the air as it passes through the heat exchanger. It should be noted that the protuberances 344 may be of different dimensions and number, and may only be on either the upper or the lower surface only.

FIG. 20 shows yet a further embodiment, in side view, of a fragrance dispenser 350, comprising a heat exchanger 352 and a housing 354 for the substance 356 providing the aromatic or fragrant aroma. The substance 356 is inserted in the housing 354, and air flows thereto from the heat exchanger 352. The heat exchanger includes a metal plate 358, and a plurality of plate extension shelves 360, which provide a pathway for the air as it is heated, thoroughly mixed, and eventually introduced into the housing 354 so as to heat the substance 356, and thereby provide the aromatic dispensation of air.

Figure 21:
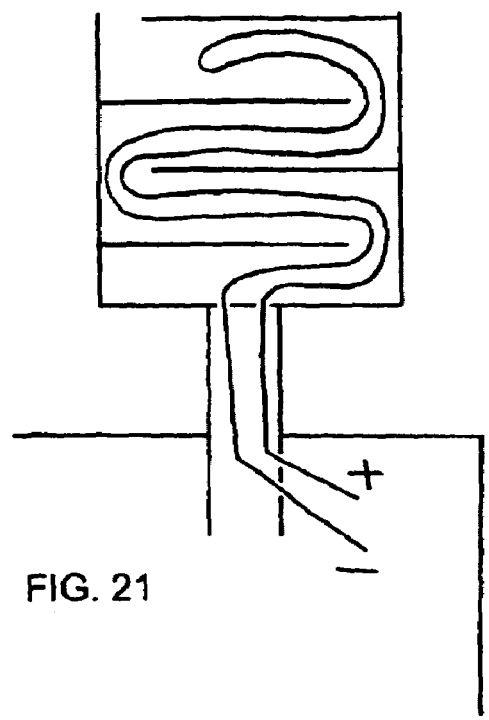
FIG. 21 is a schematic cross-section through another embodiment of the invention.

An internal heating system instead of a blow torch is shown in FIG. 21, and uses a resister coil (electric heating element) to warm up the heating element from the inside instead of the outside. The positive and negative leads of this resister coil can be attached to a battery within holder housing 18 or an external/separate battery, or by a cord, into a wall outlet.

Figure 22:
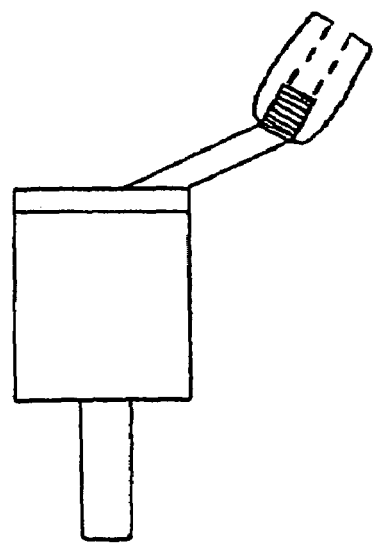
FIG. 22 is a schematic representation of another embodiment of the invention.

In FIG. 22 of the drawings, instead of having a cap 156, a permanent top with a tube screwed into a wooden mouthpiece can be used to blow air into the heating element.

The heat exchanger is preferably comprised of metal, and preferably a high purity aluminum to ensure high heat conductivity, and the ability to store heat. The base may be comprised of wood, or plastic, or some other material which does not absorb heat, and therefore will not become hot and burn the user.

The use of the heat exchanger, in conjunction with the thermometer, enables or facilitates control of the input of heat, and the consistency of the results produced. As a general guideline, and without in any way limiting the scope of the invention, the aromatic substance may burn at 20% efficiency at a temperature of about 500° F. and up. It may operate at 85% efficiency at temperatures between about 200° F. and 400° F., so that aromatization of the substance is enhanced. Also, at optimal temperatures, there will be less or reduced or no smoke, and the absence of the high heat, and/or no smoke is less likely to set off fire alarms. Also, controlling the temperature to ensure optimal aromatization may significantly reduce the production of harmful chemicals which occurs at combustion. In any event, the purposes of the consistent heating mechanism of the heat exchanger, and the monitoring of the amount of heat by the thermometer displays, enables the user to ensure sufficient heat to produce aromatization, without creating combustion and the disadvantages and perils associated therewith.

In one form, the lower plates may create more turbulence or agitation in order to transfer the same amount of heat as the top plates. As an example only, the temperature of the air may be about 74° F. when entering the top plates, while the temperature of the same air entering the lower plates is around 250° F. As such, the spacing, and configuration, of the various plates can be adjusted so that maximum efficiency in producing the necessary heat can be achieved.

The thermometer is preferably a built-in device, and may comprise a bi-metallic thermometer. The thermometer preferably measures the heat directly on the heating element.

The invention is not limited to the precise details described above, and modifications may be made in accordance with the invention.

The invention claimed is:

1. A fragrance dispenser comprising:
   a receptacle for receiving an aromatic substance to be heated;
   a heat exchanger being connectable to the receptacle for heating air to go through the receptacle, the heat exchanger having a housing having a chamber containing at least one plate forming a means for agitating the air, the plate sealing most of the heat exchanger housing from the receptacle, the plate defining an open space which causes agitation and mixing of the air by subjecting the air flow to a turn of direction.

2. A dispenser as claimed in claim 1 wherein the means for agitating the air comprises a plurality of plates.

3. A dispenser as claimed in claim 2 wherein the plates are arranged in a stacked, substantially parallel arrangement, wherein a channel is formed between adjacent plates, and the plurality of plates define an air flow path through the heat exchanger along the channels.

4. A dispenser as claimed in claim 1 wherein the heat exchanger is substantially rectangular in cross-section, and each plate is substantially rectangular in shape, the plate connecting to the heat exchanger along three of its sides.

5. A dispenser as claimed in claim 4 wherein each plate has two long sides and two short sides, and the plate connects to the heat exchanger along two long sides, and along one short side, the plate having an unconnected short side.

6. A dispenser as claimed in claim 5 wherein a gap is formed between the unconnected short side of the plate and the heat exchanger, the gap comprising a part of the flow path of the air as it passes through the heat exchanger.

7. A dispenser as claimed in claim 3 wherein the open space associated with each plate is on an opposing section of the heat exchanger relative to the open space associated with the plates adjacent thereto.

8. A dispenser as claimed in claim 1 wherein each plate has an upper and lower surface, and turbulence producing structures are formed on at least one of the upper and/or lower surfaces.

9. A dispenser as claimed in claim 8 wherein the turbulence producing structures comprise a plurality of projections extending upwardly from the upper and/or lower surface of the plate.

10. A dispenser as claimed in claim 8 wherein the turbulence producing structures comprise depressions formed in the upper and/or lower surface of the plate.

11. A dispenser as claimed in claim 2 further comprising spacers formed between adjacent plates.

12. A dispenser as claimed in claim 2 wherein the heat exchanger comprises at least one rail, and the plates comprise corresponding receivers for engaging the rail and facilitating proper orientation of the plate within the heat exchanger.

13. A dispenser as claimed in claim 8 wherein the turbulence producing structures comprise a series of transverse walls located on the upper and/or lower surface of the plate, the transverse walls producing a nonlinear flow path for at least a portion of the air flowing between adjacent plates.

14. A dispenser as claimed in claim 2 further comprising a spring connector associated with each plate, the spring connector being connectable to the plate and the heat exchanger in a releasable manner to secure the plate in the heat exchanger.

15. A dispenser as claimed in claim 1 wherein the receptacle comprises a container downstream of the heat exchanger.

16. A dispenser as claimed in claim 1 wherein the receptacle comprises a removable tray which can be inserted in the path of air discharged from the heat exchanger, the removable tray having a handle to facilitate insertion and removal of the tray.

17. A dispenser as claimed in claim 1 wherein the receptacle comprises a screen formed in a tubular extension extending from the heat exchanger.

18. A dispenser as claimed in claim 1 wherein the ejection mechanism is a spring-loaded shaft, one end of which is a adjacent the receptacle, and the other end of which comprises a button for activation by the user.

19. A dispenser as claimed in claim 1 further comprising a thermometer for monitoring and displaying the temperature in the heat exchanger.

20. A dispenser as claimed in claim 19 wherein the thermometer is a digital thermometer located in a handle housing adjacent the heat exchanger, the digital thermometer having a sensor or probe in the heat exchanger.

21. A dispenser as claimed in claim 1 further comprising a heating source external to the heat exchanger for heating air in the heat exchanger.

22. A dispenser as claimed in claim 1 further comprising an aroma dispersal container for realizable receiving at least a portion of the dispenser, the aroma dispersal container containing at least one aperture through which aromatic air produced by the dispenser can be discharged into the surrounding atmosphere.

23. A dispenser as claimed in claim 1 wherein the heat exchanger is comprised of aluminum.

24. A method for producing an aroma from an aromatic substance, comprising:
    placing the aromatic substance in a receptacle to be heated; and
    attaching a heat exchanger to the receptacle for heating air upstream of the receptacle, and agitating the air as it is heated by conveying the air over a plurality of approximately parallel plates which are staggered with respect to each other to define a flow path which subjects the heated air to shear forces; and
    passing the heated air over the aromatic substance.

25. A fragrance dispenser as claimed in claim 1 wherein:
    the heat exchanger comprising a series of plates wherein each plate has four sides, and the plate connects to the heat exchanger along three sides, the plate having an unconnected side, the plates defining a flow path for the air.

26. A dispenser as claimed in claim 1 further comprising an ejection mechanism for ejecting used aromatic substance from the receptacle.

* * * * *